United States Patent [19]

Okada et al.

[11] Patent Number: 4,935,358

[45] Date of Patent: Jun. 19, 1990

[54] INTERESTIFICATION OF FATS

[75] Inventors: Wataru Okada, Kobe; Susumu Kyotani, Takasago; Takeshi Shiotani, Kobe; Toshimitsu Nakashima, Takasago, all of Japan

[73] Assignee: Kanegafuchi Kagaku Kogyo Kabushiki Kaisha, Osaka, Japan

[21] Appl. No.: 314,277

[22] Filed: Feb. 23, 1989

Related U.S. Application Data

[63] Continuation of Ser. No. 636,956, Aug. 2, 1984, abandoned.

[30] Foreign Application Priority Data

Aug. 2, 1983 [JP] Japan .................................... 141496

[51] Int. Cl.[5] ............................................ C12P 7/64

[52] U.S. Cl. .................................. 435/134; 435/135; 435/177; 435/179; 435/254; 435/260; 435/261

[58] Field of Search ............... 435/134, 135, 254, 260, 435/261, 177, 179

[56] References Cited

U.S. PATENT DOCUMENTS

| | | | |
|---|---|---|---|
| 3,974,036 | 8/1976 | Snell | 435/174 X |
| 4,149,936 | 4/1979 | Messing et al. | 435/376 |
| 4,332,895 | 6/1982 | Griffiths et al. | 435/179 |
| 4,416,991 | 11/1983 | Matsuo et al. | 435/134 |
| 4,450,233 | 5/1984 | Mimura et al. | 435/178 |
| 4,525,457 | 6/1985 | Sakata et al. | 435/181 X |

OTHER PUBLICATIONS

Akhtar, Metal, *Pak. J. Biochem.*, vol. 9(1) pp. 1-4, 1976.

Chem. Abst. vol. 87:196959h, p. 342, 1977.

Kosugi et al., J. Ferment. Technol., vol. 49, No. 12, pp. 968-980, 1971.

MacRae, "Lipase-catalyzed Interesterification of Oils and Fats," JAOCS, vol. 60, No. 2, Feb. 1983.

*Primary Examiner*—Robert A. Wax

*Attorney, Agent, or Firm*—Armstrong, Nikaido, Marmelstein, Kubovcik & Murray

[57] ABSTRACT

A process of an interesterification reaction of fats, wherein a fatty acid moiety of a glyceride is substituted by other fatty acid moiety, and the reaction is accelerated by a catalyst and is continued constantly at a high rate for a long time. The process uses a dry cell for a catalyst. The dry cell is prepared from a lipase-containing microorganism by cultivating it to increase a lipase content and drying it to control water content.

14 Claims, 1 Drawing Sheet

INTERESTIFICATION OF FATS

This application is a continuation of application Ser. No. 636,956, filed Aug. 2, 1984.

BACKGROUND OF THE INVENTION

The present invention relates to a process of interesterification reaction of fats, wherein the rate of interesterification reaction is increased and the reaction is continued constantly at a high rate for a long time, and more specifically, to a form of the lipase enzyme which exhibits a catalytic action to the interesterification reaction, which is, to a dry cell which contains the lipase enzyme in itself.

Hitherto, there have been used an alkaline metal, and the alkoxylate and the hydroxyl compound thereof as a catalyst in the interesterification reaction of the fats. But those catalysts do not have the specificity to react specific positions of glycerides. Recently, the lipase enzyme is used as a catalyst in the reaction, e.g. when the lipase enzyme acts on a mixture of the fat and the fatty acid, the interesterification (also known as transesterification) reaction is carried out at a specific position according to the characteristics of the enzyme. By using such a method, various fatty acids were subjected to the interesterification according to the various purposes [cf. Japanese Unexamined Patent Publication (Tokkyo Kokai) No. 104506/1977, Japanese Examined Patent Publications (Tokkyo Kokoku) No. 6480/1982, No. 27159/1982 and No. 28519/1982]. However, in case of using an enzyme as a catalyst, which does not exhibit activity until dissolved in water or in the presence of water, on a substrate (a reactant) immiscible with water such as a fat or a fatty acid, there are some problems as follows:

(1) For the purpose of increasing a rate of contact between the substrate and the enzyme, it is desirable to add the enzyme directly to the substrate. However, the enzyme is rapidly inactivated in the fats or organic solvent unless it is protected in some manner. In the above-mentioned Patent Publications, a method is disclosed, wherein the enzyme is adsorbed to a carrier such as an adsorbent to prevent inactivation. But the enzyme rapidly loses its activity, as soon as it is desorbed from the carrier.

(2) When there is too great and amount of water in the vicinity of the enzyme, the hydrolysis (saponification) reaction becomes dominant and the interesterification reaction hardly proceeds 0n the contrary, when the amount of water is too small, though the interesterification reaction certainly proceeds, a rate of reaction is very slow and the enzyme loses its activity. There are described the amounts of water suitable for the interesterification reaction of 0.2 to 1.0% by weight in Japanese Unexamined Patent Publication No. 104506/1977, 0.005 to 0.18% by weight in Japanese Examined Patent Publication No. 27159/1982 and 0.01 to 0.20% by weight in Japanese Examined Patent Publication No. 28519/1982, respectively. There is also disclosed in Japanese Examined Patent Publication No. 6480/1982 that the interesterification reaction can be carried out without hydrolysis when lower alcohols of 2 or 3 hydroxyl groups are used in place of water. However, according to the inventors' experience, the rate of reaction is small in those methods and they are poor in practical use.

(3) With respect to the method, wherein the enzyme is adsorbed to a carrier of an adsorbent, reactants can hardly diffuse to the enzyme on the carrier, and especially, the enzyme adsorbed into fine pores of the carrier substantially cannot take part in the reaction, and therefore an amount of the effective enzyme is decreased. Such a tendency becomes more striking as a more hydrophilic carrier is used.

As mentioned above, in case of conducting the interesterification reaction, wherein the lipase enzyme which exhibits an activity in an aqueous system is reacted as a catalyst with an oily reactant, it is necessary not to inactivate the enzyme, to control an amount of water in the vicinity of the enzyme in a suitable amount and not to decrease the rate of contact between the enzyme and the reactant Every Patent Publication described above mainly pays attention to the above-mentioned problem (2) only and has little regard for the problems (1) and (3). However, the problems (1) and (3) are very important subjects for the interesterification system, wherein the reactant and the enzyme consist in the different phases, respectively, and the enzyme is under a condition that it is easy to lose its activity.

It is an object of the present invention to solve the above-mentioned problems and to carry out the interesterification reaction rapidly without inactivating the enzyme over an extended period.

Those and other objects of the present invention will become apparent from the description hereinafter.

SUMMARY OF THE INVENTION

In accordance with the present invention, there is provided a process of an interesterification reaction of fats and oils comprising glycerides, wherein the fatty acid moieties of the glycerides are substituted by other fatty acid moieties by suspending dry cells containing lipase and having a water content of 1 to 20% by weight of the dry cell into a mixture of the glyceride and the other free fatty acid.

The present invention also relates to a dry cell employable in the above-mentioned process, i.e. the dry cell which is obtained by cultivating a microorganism containing lipase where at the beginning or on the way of the cultivation is added a glyceride or a fatty acid as a lipase inducer 1 to 80% by weight in culture solution, washing the obtained microorganism with a watersoluble solvent, and then, drying the microorganism to a water content of 1 to 20% by weight of the dry cell.

DETAILED DESCRIPTION

Figure 1:
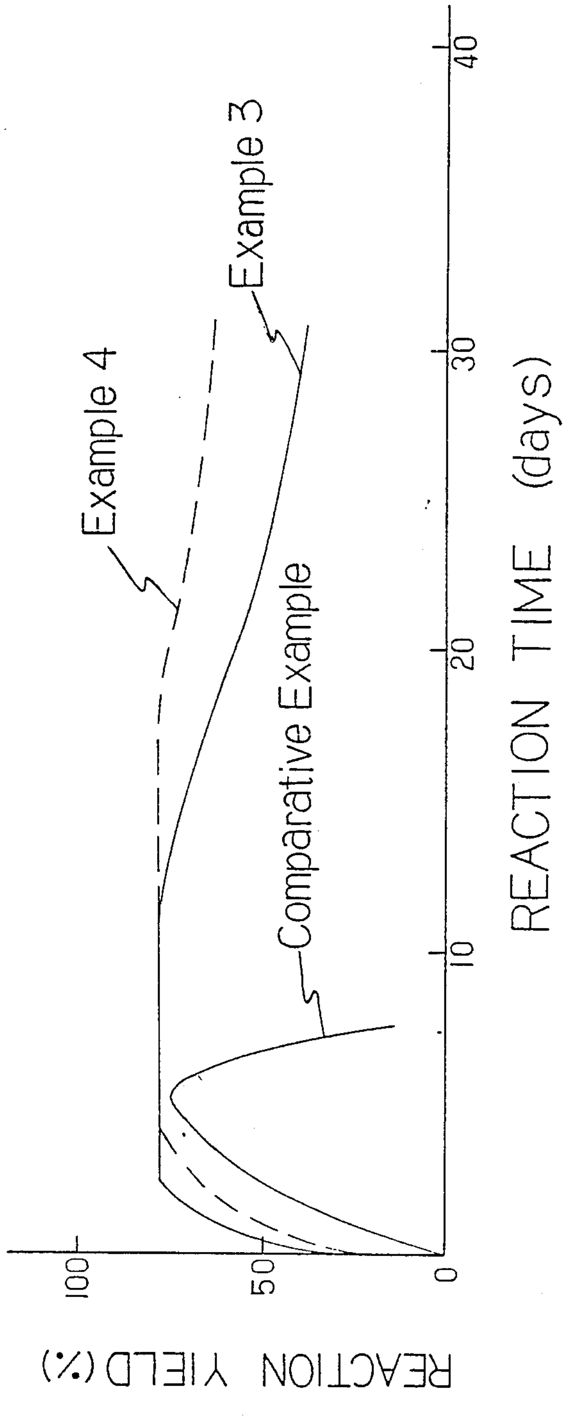
FIG. 1 is a graph showing a change in a reaction yield in relation to a reaction time.

In accordance with the present invention, there is used a customary animal fat, vegetable oil or synthetic oil as the fats. Typical examples of such a fat or oil are, for instance, olive oil, palm oil, shea butter, soybean oil, cotton seed oil, beef tallow, lard, fish tallow, and the like.

The fatty acid usable in the present invention is a fatty acid having 8 to 20 carbon atoms of a natural product. Typical examples of such a fatty acid are, for instance, stearic acid, palmitic acid, oleic acid, linoleic acid, and the like. When a saturated fatty acid of high carbon atoms, which has a high melting point of 60° to 80° C., is used, there can be used as a solvent to dissolve the fatty acid a hydrocarbon such as hexane or heptane; an ether such as ethylether or propylether; an ester such as methyl acetate or ethyl acetate; benzene; acetone; and the like. The dry cell of the present invention does not lose its activity and can act as a catalyst in the exemplified solvents.

The dry cell used in the present invention is prepared from any microorganism which produces lipase Typical examples of such a microorganism suitable for the present invention are, for instance, microorganisms belonging to a genus Rhizopus, Mucor, Aspergillus, Candida, Geotrichum, and the like.

For the purpose of preparing the exemplified microorganism effectively as a catalyst, it is important to cultivate the microorganism so that the microorganism contains a large amount of lipase in its body and to dry the cultivated microorganism so that lipase in the microorganism can easily come in contact with the fats or the fatty acids.

It is the second aspect of the present invention to provide a dry cell employable in the interesterification reaction of fats as a catalyst.

In accordance with the present invention, there can be obtained a dry cell which has an action to accelerate the interesterification reaction and to keep the reaction rate constantly high for a long time, by cultivating a microorganism containing lipase where at the beginning or on the way of the cultivation is added a glyceride or a fatty acid as an inducer for inducing lipase 1 to 80% by weight in culture solution, washing the obtained microorganism with a water-soluble solvent, and then, drying the microorganism to a water content of 1 to 20% by weight of the dry cell.

In the above cultivation, mono, di or triglycerides, fatty acids having 8 to 20 carbon atoms or the esters thereof can be used as an inducer for inducing lipase. Among those, triolein (olive oil), diolein, monoolein, oleic acid and linoleic acid, which change their form into a liquid state at a common cultivating temperature (20° to 40° C.), are preferably used. An added amount of the inducer is suitably an amount to give a concentration of 1 to 80% by weight in the culture solution. When the added amount of the inducer is not more than 1% by weight, the lipase content in the microorganism body is lowered and a rate of interesterification reaction becomes very small. When the added amount of the inducer breaks 1% by weight, the lipase content in the microorganism body begins to increase abruptly to show a maximum lipase content at the amount of the inducer of 5 to 10% by weight. When the amount of the inducer is further increased, more than 40 to 50% by weight, the culture system forms a W/O emulsion, and the microorganism multiplies in water drops and accumulates lipase in its body. An activity of lipase contained in the microorganism obtained by cultivating in the above-mentioned W/O emulsion is still high and the microorganism can be sufficiently employed in the interesterification reaction. However, when the amount of the inducer is greater than 80% by weight, the yield of the dry cell is lowered as a result of decreasing the culture solution, and therefore, it is not suitable for a practical use.

An activity (a content) of lipase in the microorganism body changes greatly according to the cultivating time, and it is necessary to stop the cultivation at the time when the activity shows a maximum value. The time showing the maximum peak of the activity almost agrees to the time when a nutrition source, especially a carbon source is totally consumed. Therefore, with respect to the cultivation of the microorganism, it is desirable to stop cultivation when the nutrition source has been consumed and the autolysis of the microorganism begins.

As a method of removing water from the thus obtained microorganism, the microorganism can be dried at a temperature that it does not lose its activity (not more than 40° to 60° C.) as a rule.

But when simply the water is evaporated, a shrinkage of the cellular tissues takes place to make the microorganism very hard and the contact between lipase in the cellular tissues and the substrates out of the cellular tissues is impeded, and therefore, the activity of lipase cannot appear. Consequently, when the microorganism is dried, it is necessary to employ a drying method, in which the cellular tissues are not shrunk. For that purpose, the microorganism is soaked in a water-soluble solvent, for instance, acetone, a lower alcohol such as methyl alcohol, ethyl alcohol or iso-propyl alcohol, or the like to replace the water in the cellular tissues with the solvent, and then, the solvent is evaporated to give a dry cell, which is kept from the shrinkage of the cellular tissues In that case, a vacuum dry is preferable as a drying method. On the contrary, when the use of the solvent is not desirable, a freeze dry may be employed Moreover, the shrinkage of the cellular tissues can be further avoided by fixing the tissues by soaking the microorganism in an aqueous solution of glutaraldehyde having a concentration of less than 5% by weight of the aqueous solution before soaking in the solvent as exemplified above, whereby a more preferable dry cell can be prepared. When the concentration of the aqueous solution of glutaraldehyde is not less than 5% by weight, a degree of crosslinking becomes too high and the rate of interesterification reaction is lowered, and therefore, the concentration is preferably less than 5% by weight.

It is necessary to dry the cultivated microorganism so that the water content is 1 to 20% by weight in the microorganism from the viewpoint of inhibiting a hydrolysis reaction. When the water content is greater than 20% by weight, the hydrolysis is dominant rather than the interesterification reaction and the hydrolyzed products such as diglyceride, monoglyceride and glycerine take the greater part of the total products On the contrary, the water content is preferably as small as possible, and it does not particularly need to claim the lower limit. But, in a common drying method, the water content cannot decrease below equillibrium water content of the drying material. In that sense, it is difficult to dry the microorganism under the vacuum condition at room temperature so that the water content is not more than 1% by weight The dry cells prepared by the method as described above generally have the water content of 1 to 5% by weight. A control of the water content can be easily achieved by varying the drying time.

An added amount of the thus prepared dry cell into the reactants (a mixture of the glyceride and the fatty acid) to give a suspension is preferably an amount so that a water content of the reaction system (a mixture of the glyceride, the fatty acid and the dry cell) is 0.1 to 10% by weight. When the amount is not more than 0.1% by weight, an amount of lipase in the reaction system is small and the reaction rate is lowered, and therefore, the process is not suitable for a practical use. When the amount is greater than 10% by weight, the reaction rate is certainly increased, but the viscosity of the reaction system is also increased to make the mixture state worse and the reaction is not accelerated in proportion to the added amount, and further, the separating operation to recover the dry cell after the reaction is difficult. An added amount is more preferably an amount so that a water content of the reaction system is 1 to 5% by weight from the viewpoint of the reaction rate and the operation.

In a conventional method in which the enzyme is adsorbed to the carrier, the hydrolysis cannot be repressed unless a water content in the reaction system is controlled to be not less than 1% by weight. On the contrary, it was found that by the process of the present invention, the interesterification reaction can be carried out at a high rate while repressing the hydrolysis almost completely even in the reaction system having a water content more than 1% by weight. That is, it is supposed that though an apparent water content in the dry cell is large, an amount of water which participates in the reaction is considerably smaller than the apparent water content. It is not clear in what form the water which does not participate in the reaction is present in the dry cell, but the water is thought to contribute to a stabilization as well as an activation of the enzyme, because the inactivation rate of lipase enzyme in the dry cell by the present invention is far smaller than that by conventional methods with immobilized enzyme, and the dry cell can be satisfactorily used for a long enough time. Essentially, an enzyme is a biogenic catalyst and has a property that it acts well in moderate surroundings and easily loses its activity in radical surroundings Moreover, a reactivation of enzyme is difficult once it was inactivated. In particular, in oil-water phase system as seen in the present interesterification reaction the enzyme is under a condition that it always contacts with the oil phase, and so in radical surroundings. In just such a case, it is an important subject whether the enzyme activity can be maintained for a long time or not. The process of the present invention is satisfactory in that respect.

The advantages of the present invention can be summarized as follows:

(1) Because lipase in the dry cell is under protections of the cellular tissues and the water in the tissues, the inactivation rate of lipase is small and the dry cell can be used in the interesterification reaction for a long time;

(2) The enzyme activity can be further enhanced by increasing the water content in the dry cell;

(3) The reaction rate in the present invention is 2 to 5 times greater than that in the conventional method in which the lipase enzyme is adsorbed on the carrier under the condition of the same units of lipase enzyme, probably because lipase in the dry cell or the vicinity thereof is thought to have a good affinity for a fatty substrate;

(4) A decrease of the enzyme activity cannot be observed even when the reaction is carried out in a solvent such as hexane; and (5) The dry cell has a strong tolerance against a pH or temperature change.

An enzyme itself has a restriction about pH and/or a temperature to exhibit its activity. For example, *Rhizopus delemar* lipase acts well at pH of 4 to 7 and a temperature of 30° to 40° C., and lipase is inactivated or the activity is considerably lowered in the other conditions. On the contrary, lipase in the dry cell of the present invention, of course, shows a stable activity in the above surroundings, and moreover, the enzyme activity is not lowered to so much extent and is maintained even in the other conditions. The reason is thought to maybe come from the above-mentioned advantage (1). An extending advantage from the advantage (1) is the fact that the reaction can be accelerated by elevating a reaction temperature (for instance, 50° to 60° C.).

Lipase in the dry cell of the present invention has advantages as described above. Moreover, the reaction temperature can be elevated to 70° C. when a thermostable (thermophilic) stain is used as a lipase-producing strain. Typical examples of such a thermostable strain are strains belonging to the genus Rhizopus, for instance, *Rhizopus chinensis, Rhizopus pseudochinensis, Rhizopus hamillis,* and the like. For example, a thermostable strain belonging to *Rhizopus chinensis* can grow up at a temperature up to 50° to 60° C. When a dry cell is prepared from such a strain by this cultivating method according to the present invention, the obtained dry cell can be employed to an interesterification reaction which is carried out at a temperature over 70° C. A fatty acid such as stearic acid or palmitic acid has a melting point of 68° to 72° C. When the reaction can be carried out at a temperature over 70° C. as described above, it is advantageous that the solvent to dissolve the fatty acid having such a melting point can be without.

When a microorganism which contains lipase having a 1,3-specificity is applied to the present invention, it is also possible to interesterify in the 1- or 3-position of the glyceride selectively. Typical examples of the microorganism which produces lipase having a 1,3-specificity are, for instance, the microorganisms selected from the genus Rhizopus such as *Rhizopus delimor* or *Rhizopus chinensis; Mucor japonicus; Aspergillus niger;* and the like.

Further, at a time of cultivating the microorganism containing lipase in a culture solution, when porous particles having diameters of 50 to 2000 μm are added in the culture solution in an amount of 5 to 30% by weight of the culture solution before the cultivation of the lipase-producing microorganism, the microorganism multiplies in the pores of the paricles, and at last the surface of the particle is covered by the microorganism. By drying the thus obtained immobilized microorganism according to the present invention, the immobilized microorganism capable for the interesterification reaction can be prepared. In that case, the enzyme fixed to the particle is more stable and the continuous operation of the interesterification reaction can be possible. For example, with respect to the continuous operation of the interesterification reaction which employs the immobilized microorganism, the enzyme activity is stable for 1 to 2 weeks, and greater than 60% of the activity remained 1 month later.

The present invention is more specifically described and explained by means of the following Examples. It is to be understood that the present invention is not limited to the Examples, and various changes and modifications may be made in the invention without departing from the spirit and scope thereof.

EXAMPLE 1

*Rhizopus delemar* was subjected to the aerated cultivation at 30° C. and pH 5.6 for 50 hrs in the medium whose composition is shown in Table 1, wherein the olive oil is an inducer.

TABLE 1

| Ingredients | Content (%) |
|---|---|
| Peptone | 7 |

TABLE 1-continued

| Ingredients | Content (%) |
|---|---|
| Glucose | 2 |
| $MgSO_4.7H_2O$ | 0.05 |
| $NaNO_3$ | 0.1 |
| $KH_2PO_4$ | 0.1 |
| Olive oil | 2 |

The obtained microorganism was washed twice with pure water and soaked in a 50% aqueous solution of acetone for 10 mins, and then, into a 100% aqueous solution of acetone for 5 mins. Then, the solution was filtered and the microorganism was dried under a vacuum condition at 30° C. for 2 hrs. A water content of the thus obtained dry cell was about 5% by weight. An enzyme activity was 20,000 units/g of a dry cell.

An interesterfication reaction, the reaction system of which is as shown in Table 2, was carried out using the obtained dry cell.

TABLE 2

| Ingredients of the reaction system | Amount (g) |
|---|---|
| Hexane | 20 |
| Olive oil | 10 |
| Stearic acid | 10 |
| Dry cell | 10 |

The reaction was carried out at 40° C. for 48 hrs with stirring to complete. The obtained products are shown in Table 3.

TABLE 3

| Products (the fatty ingredients) | Amount (g) |
|---|---|
| 1,3-stearo-2-oleotriglyceride | 6.0 |
| 1-stearo-2,3-dioleotriglyceride | 2.0 |
| Olive oil | 1.5 |

Oleic acid moieties at 1- and 3-positions were substituted with stearic acid moieties, respectively, because lipase in *Rhizopus delemar* has a 1,3-specificity.

As for 80% of olive oil, the interesterification reaction occurred at 1-position or at 1- and 3-positions, and 5% of olive oil was converted to a diglyceride. If a water amount in the vicinity of the enzyme is large, hydrolysis proceeds and olive oil is decomposed into a diglyceride and further to a monoglyceride. On the contrary, in the present Example, a rate of hydrolysis was lowered to 5%.

EXAMPLE 2

The procedure of Example 1 was repeated except that a thermostable strain of *Rhizopus chinensis* was used instead of *Rhizopus delemar* to give a dry cell. Then, the interesterification reaction was carried out according to the procedure of Example 1 except that the reaction temperature was 40° C., 50° C. or 60° C., and the time necessary for completion of reaction was compared to one another. As the result, the reaction time was 45 hrs, 30 hrs and 24 hrs when the reaction temperature was 40° C., 50° C. and 60° C., respectively, i.e. a reaction rate at a temperature of 60° C. was increased almost 2 times that at a temperature of 40° C.

EXAMPLE 3

The rate of inactivation of the enzyme was measured by conducting the interesterification reaction in continuous system (flowing system) using the dry cell obtained in Example 1 as follows: Reactants and the dry cell were charged in the reactor as shown in Table 2. A substrate mixture that stearic acid was dissolved in olive oil and hexane, which has the same composition as shown in Table 2, was supplied to the reactor at a constant flow rate, while the product was taken out of the reactor at the same flow rate of the feed rate. The feed rate was also controlled so that the mean residence time in the reactor is 24 hrs. An exit was provided with a filter so that the dry cells did not flow out from the exit. The reaction temperature was 40° C.

A composition of the so-obtained product liquid was measured and the rate of inactivation of the enzyme was evaluated from the changes in a reaction yield (a rate of interesterification reaction). The result is shown in FIG. 1. As is clearly seen in FIG. 1, a steady state was continued for a week from the time when the reaction reached the steady state. After that, a reaction yield began to decrease gradually and the enzyme activity was lost little by little, but the enzyme had yet an activity not less than 40% even at 1 month later.

EXAMPLE 4

*Rhizopus chinensis* was cultivate for 50 hrs in the cultural medium having the composition shown in Table 1, in which were suspended commercially available porous sponge particles (a 1 mm cube, a porosity size: 50 to 100 μm, a void volume: about 80%). The microorganism multiplied also in the particles to cover the surfaces of the particles. The obtained particles were dried according to the present invention to fix the cells to the particles, whereby the immobilized microorganism was obtained. The procedure of Example 3 was repeated except that the immobilized microorganism was used in an amount of 20% by weight of the reaction system instead of the dry cell of Example 1 to measure the rate of inactivity of the enzyme. The result is shown in FIG. 1. As clearly seen in FIG. 1, a steady state was further continued than that in Example 3, for close to 2 weeks, and the inactivation rate was also slow.

COMPARATIVE EXAMPLE

The procedure of Example 3 was repeated except that a commercially available conventional catalyst that *Rhizopus delemar* lipase was adsorbed to sellaite was used instead of the dry cell of Example 1 to measure the rate of inactivity of the enzyme. The result is shown in FIG. 1. As is easily understood from FIG. 1, the steady state continued only for 2 to 3 days and the enzyme activity was lowered to 20% at 1 week later.

In addition to the ingredients used in the Example, other ingredients can be used in the Example as set forth in the specification to obtain substantially the same results.

What we claim is:

1. A process for the interesterification of glycerides and fatty acids wherein a fatty acid moiety of a glyceride is exchanged with a fatty acid moiety of free fatty acid comprising:

(a) soaking cells containing lipase in a water-soluble solvent;

(b) drying said cells by evaporation to a water content between 1 and 20% by weight of the cells, thereby making dry cells;

(c) suspending said dry cells in a reaction mixture consisting essentially of a glyceride, a fatty acid, and a solvent therefor, the amounts being adjusted so that the amount of water in the reaction mixture is 0.1 to 10% by weight; and (d) reacting said dry cells in a reaction mixture for a period sufficient to achieve interesterification at a temperature of 20° to 60° C., wherein a mixing ratio of a glyceride and a fatty acid is 1:1 by weight and a ratio of solvent and the sum of glyceride and fatty acid is 1:1 by weight.

2. A process according to claim 1 further comprising cultivating the cells in the presence of 1 to 80% by weight, based on the weight of culture solution, of a lipase inducer prior to step (a) to accumulate lipase in the cells.

3. A process according to claim 2, wherein the lipase inducer is selected from the group consisting of glycerides and fatty acids.

4. A process according to claim 1, wherein the concentration of said dry cells in the reaction mixture is adjusted so that the amount of water in the reaction mixture is 1 to 5% by weight.

5. A process according to claim 1, wherein said dry cells are prepared from a microorganism selected from the group consisting of the genus Rhizopus, Mucor, Aspergillus, Candida and Geotrichum.

6. A process according to claim 5, wherein said dry cells are prepared from a microorganism which is a thermostable strain selected from the genus Rhizopus.

7. A process according to claim 1, wherein said dry cells contain lipase having 1,3-specificity.

8. A process according to claim 7, wherein said dry cells containing lipase having 1,3-specificity are prepared from a microorganism selected from the group consisting of the genus Rhizopus, Mucor and Aspergillus.

9. A process according to claim 1, wherein the water-soluble solvent is acetone.

10. A dry cell containing lipase which is prepared by (a) cultivating a microorganism in a culture solution containing 1 to 80% by weight of a lipase inducer selected from the group consisting of glycerides and fatty acids, (b) washing the cultured microorganism with a water-soluble solvent; and (c) drying the microorganism to a water content of 1 to 20% by weight.

11. A dry cell according to claim 10, wherein the cultivation is stopped at the time when a carbon source in the solution is consumed, and the microorganism is recovered.

12. A dry cell according to claim 10, wherein said lipase inducer is selected from the group consisting of triolein, diolein, monoolein, oleic acid, linoleic acid and admixtures thereof.

13. A dry cell according to claim 10, wherein the microorganism is cultivated in a culture solution containing porous particles having diameters of 50 to 2000 μm in an amount of 5 to 30% weight of the medium, whereby the microorganism multiplies in the particles and becomes fixed to the particles before drying.

14. A dry cell according to claim 10, wherein the water-soluble solvent is acetone.

* * * * *